United States Patent [19]

Schiller

[11] Patent Number: 5,177,353
[45] Date of Patent: Jan. 5, 1993

[54] FINGER SURFACE IMAGE ENHANCEMENT HAVING LIQUID LAYER ON FINGER TOUCHING SURFACE OF THE PLATE

[75] Inventor: Michael Schiller, North White Plains, N.Y.

[73] Assignee: Retrievex, Inc., Bronx, N.Y.

[21] Appl. No.: 728,638

[22] Filed: Jul. 11, 1991

Related U.S. Application Data

[63] Continuation-in-part of Ser. No. 561,340, Jul. 31, 1990, Pat. No. 5,051,576.

[51] Int. Cl.⁵ .............................................. H01J 5/16
[52] U.S. Cl. ................................ 250/227.11; 250/556; 356/71
[58] Field of Search .............. 250/227.11, 227.31, 250/227.32, 556; 356/71; 382/4, 5

[56] References Cited

U.S. PATENT DOCUMENTS

| | | | |
|---|---|---|---|
| 4,322,163 | 3/1982 | Schiller | 356/71 |
| 4,414,684 | 11/1983 | Blonder | 382/4 |
| 4,428,670 | 1/1984 | Ruell et al. | 356/71 |
| 4,537,484 | 8/1985 | Fowler et al. | 382/4 |
| 4,544,267 | 10/1985 | Schiller | 356/71 |
| 4,728,186 | 3/1988 | Equich et al. | 356/71 |
| 4,783,167 | 11/1988 | Schiller et al. | 382/4 |
| 4,787,742 | 11/1988 | Schiller et al. | 356/71 |
| 4,905,293 | 2/1990 | Asgi et al. | 356/71 |
| 4,924,085 | 5/1990 | Kato et al. | 250/227.31 |
| 4,925,300 | 5/1990 | Rachlin | 356/71 |
| 4,977,601 | 12/1990 | Bicz | 356/71 |
| 5,051,576 | 9/1991 | Schiller | 250/227.11 |

Primary Examiner—David C. Nelms
Assistant Examiner—S. Allen
Attorney, Agent, or Firm—McAulay Fisher Nissen Goldberg & Kiel

[57] ABSTRACT

A layer of liquid, such as alcohol, water or a mixture thereof, on the finger touching surface of a platen provides an image in an optical fingerprint imaging system which assures valley and ridge definition and continuity by virtue of the liquid filling in the cracks and holes in the ridge zone, by creating an air pocket in the valley zone that holds the valleys open and by otherwise interacting with the finger to reinforce the distinction between valley and ridge zones in the optically imaged picture. Multiple interrogating light beams, each incident at greater than the critical angle on the finger touching surface of the platen assure imaging all minutia and that the valley zones in the image will be black. The technique is useful for roll prints and touch prints.

8 Claims, 1 Drawing Sheet

FINGER SURFACE IMAGE ENHANCEMENT HAVING LIQUID LAYER ON FINGER TOUCHING SURFACE OF THE PLATE

RELATED APPLICATIONS

This application is a continuation-in part of patent application Ser. No. 561,340 filed on Jul. 31, 1990 now U.S. Pat. No. 5,051,576 and entitled: Finger Surface Image Enhancement.

BACKGROUND OF THE INVENTION

This invention relates in general to an optical apparatus for generating a finger image and more particularly to such an apparatus which provides an image with improved ridge and valley definition.

A number of techniques are known for optically reading a finger surface to provide an image which is the equivalent of an inked fingerprint. These techniques include a direct finger imaging technique described in U.S. Pat. No. 4,787,742 issued Nov. 29, 1988 and entitled Direct Finger Reading and the use of a curved platen in order to take into account the effect of the maximum angle of refraction on a platen as shown in U.S. Pat. No. 4,783,167 issued Nov. 8, 1988 and entitled Finger Imaging Apparatus Using Curved Platen.

The desired result is a fingerprint image with the ridges and valleys clearly shown so that ridge and valley end points and bifurcations can be identified to provide unique identification points for each finger. These identification points are called minutia and they provide a unique identification of the individual involved.

A major problem is that the ridges contain cracks and holes which create a non-continuous, non-smooth ridge line that tends to make automatic identification of the line ending and line bifurcation minutia more difficult. Complex mathematical techniques can be employed to heal some of these ridge defects. However, both for the purpose of visual examination of the image generated as well as from the point of view of automatic identification point determination, it is desirable to provide an image in which these ridge defects are minimized.

Another problem is that certain valleys close down under pressure of a finger on a platen thereby losing some definition and some minutia.

Accordingly, it is a major purpose of this invention to provide a technique in which the image of the ridges will bridge over the cracks, holes and discontinuities in the ridges as much as possible so as to provide a simplified fingerprint image for viewing and processing and in which the valleys will be held open so that a distinctive ridge/valley image can be formed.

BRIEF DESCRIPTION

In brief, one embodiment of this invention employs a glass platen having a flat finger touching surface on which a layer of water is deployed. A finger immersed in the water and pressed against the surface causes the water to fill in the cracks of the ridge portions of the finger surface and also to flow partly up into the valley portions of the finger surface. Enough air is trapped in the valley portions so that the water does not fill the valley portions and an air pocket is created to hold the valleys open.

One or more collimated interrogating light beams illuminate the finger. The angle of incidence of the light rays in the interrogating light beam to the finger touching surface of the platen are at an angle to the normal greater than the maximum angle of refraction (MAR). The MAR equals 41.2 degrees for glass. The liquid, in this case water or alcohol or a mixture thereof, preferably has an index of refraction which approximates that of the glass platen. In any case, if the maximum angle of refraction (MAR) for the liquid is greater than that for glass, then the angle of incidence of the interrogating light beam rays should be equal to or greater than the liquid MAR value. The ridges contact the platen and are immersed in the liquid so that a three-dimensional ridge zone extends from the platen contact up to the level of the liquid in the valleys. The ridge zone reflects light in a scattered fashion. The scattered light is focused by an imaging lens to form a light image of the ridge zones on a photo-electric transducer optically downstream from the finger surface.

The level of the liquid in the valleys is above the surface of the platen. The light incident on the liquid-to-air interface at the valleys is reflected as a mirror reflection. Because the incident angle of the interrogating light beam rays is greater than the MAR, the reflected light from the valley zones emerges out the sides of the platen. Accordingly, the valley zones are a black image at the photo-electric transducer.

Since the incident light is at a very substantial angle to the normal, scattered light from the ridge zone is from the portion of the ridge in contact with the glass platen and that side of the ridge which faces the incident interrogating light beam. The other side of the ridge may be illuminated by an additional light beam. The scattered light which is imaged on the array of photo electric-transducers downstream is of that portion of the ridge from which light is scattered.

This layer of water provides an enhanced image in the system where a finger is rolled across the platen to obtain a so-called "nail-to-nail print" as well as the system involving a touch contact of a finger on the platen. It has been noted that in the finger roll system, the employment of the liquid substantially reduces the slip or slide problem that occurs with a dry platen.

BRIEF DESCRIPTION OF THE DRAWINGS

FIG. 2 is a view looking at the tip of the finger and illustrates the optical relationship of one of the two light sources to the platen and finger.

FIG. 4 shows the air pockets 36 which defines the valley zones and also shows the liquid zones, between air pockets, which define the ridge zones.

DESCRIPTION OF THE PREFERRED EMBODIMENTS

Apart from the platen itself, some of the arrangement and structure of the system for which this invention is an improvement is shown and described in U.S. Pat. No. 4,783,167 and that disclosure is incorporated herein by reference including the definitions in that patent for "Optical Axis", "Reading Light Beam", "MAR, (Maximum Angle of Refraction)" and "Critical Angle". The critical angle is the MAR angle derived from the relationships dictated by Snell's law.

Figure 2:
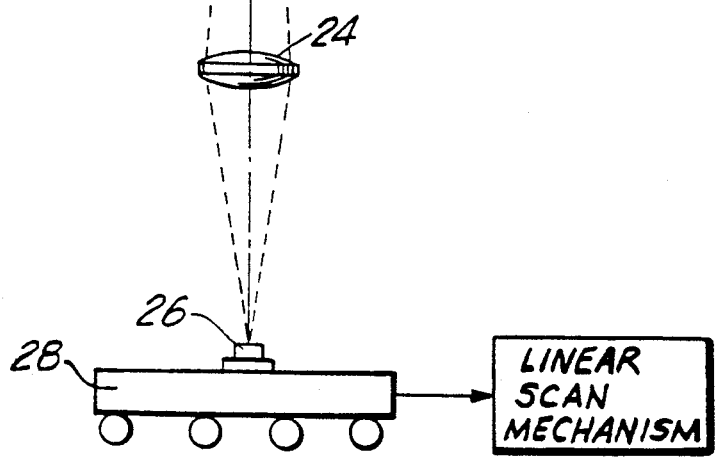
FIG. 2 is a side view of the FIG. 1 embodiment along the plane 2—2 in FIG. 1.

With reference to the FIGS., first and second light sources 10 and 12, diffuser elements 14 and collimating lenses 16 form first and second interrogating light beams 18 and 20. These interrogating light beams 18, 22, flood the finger surface that is placed against the flat back surface (finger touching surface) 22b of the platen 22. These light beams 18, 20 are modulated by the ridges and valleys of the finger F such that reflected light 23 can be focused by the spherical imaging lens 24 onto the plane of a photo-diode array 26. A charge couple diode (CCD) array 26 is a preferred type. The CCD array 26 is a linear array that is perpendicular to the plane of FIG. 2. In the embodiment illustrated, the array 26 together with the imaging lens 24 is mounted onto a slide table 28 that effects the scan of the image.

The interrogating light beams 18, 20 have the optical axes 30,32 respectively. The modulated rays that are within the aperture of the lens 24 are focused by the lens 24 on the CCD array. It is this portion of the light that is designated as the imaging light 23 and it has the axis 33, which is the axis of the lens 24.

The lens 24 and CCD array 26 are mounted on a slide table 28 designed to provide precision linear motion. A standard linear scale encoder attached to the table 28 causes the CCD array 26 to be interrogated by the downstream electronics at regular predetermined scan locations. It is preferred that the lens 24 be mounted to the slide table 28 in addition to the array 26 in order to preserve on-axis imaging at all scan positions.

Figure 4:
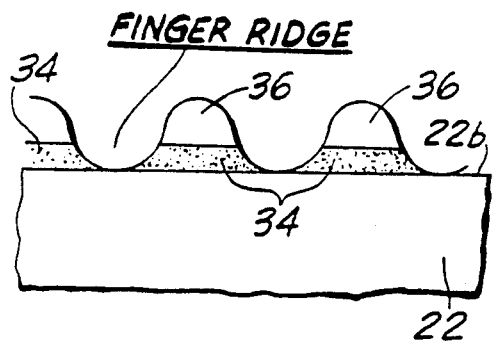
FIG. 4 is an enlarged cross-sectional view in highly schematic form of a couple of ridges of the finger pressed against the platen 22 showing the liquid 34 in schematic form.
Figure 3:
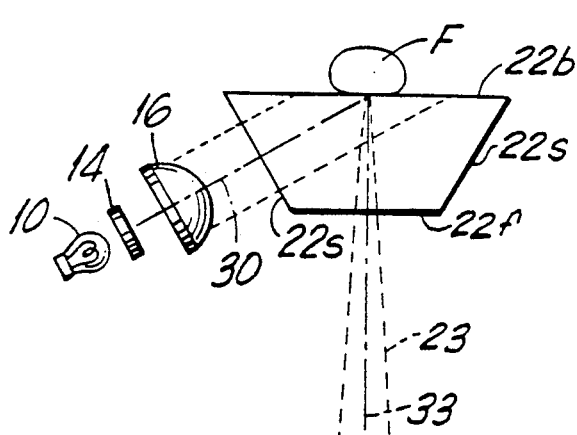
FIG. 3 is a side view along the plane 3—3 of FIG. 1 showing a side of the finger and the optical relationship of the second light source to the platen and finger.
Figure 3:
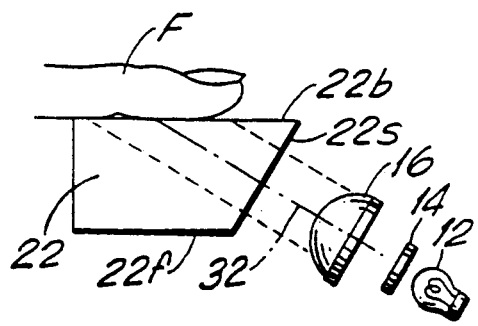

A liquid layer 34 is on the finger touching surface 22b of the platen 22. A substantial portion of the ridges of the finger F are immersed in this liquid. This creates a liquid zone that flows into most of the cracks and holes in the ridges. The result is a filled in ridge object which is imaged at the CCD array of transducers 26. FIG. 4 schematically represents the relationship between finger ridge and valley and liquid 34.

Figure 1:
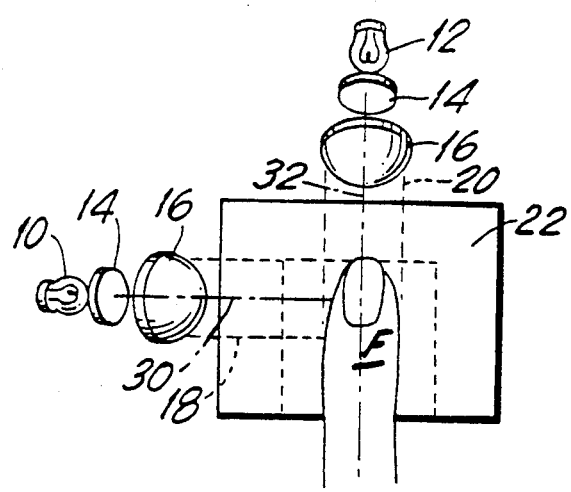
FIG. 1 is an optical and mechanical schematic representation of a plan view of an embodiment of this invention employing two interrogating light beams 18, 20 along the axes 30, 32 and an imaging light 23 within the aperture of the lens 24 having the axis 33. In this embodiment, the horizontal projections of the axes of the two light beams are at right angles to one another.

The platen 22 illustrated is for use with a single figure that is rolled from nail to nail to provide the modulated image that is focused by the lens 24. In one embodiment, that platen 22 is approximately one inch thick. It has a back surface 22b with a length of about three inches in the direction along which the finger rolls; that being the horizontal length shown in FIG. 1. The side walls 22s are angled walls at an angle of approximately 60° to the back surface 22b. Accordingly the surface 22f, from which the modulated light 23 emerges, has a length in the plane of FIG. 1 of about two inches. It is this latter relationship which assures that the light reflected from the valley zones 36 is steered away from the imaging lens 24 so that the image received by the array 26 is one with bright ridges and black valleys.

The platen 22 can be a single material glass or plastic unit or it can be layered such as shown at FIG. 5 of applicant's U.S. Pat. No. 4,322,163.

The interrogating light beams 18, 20 are collimated by the lenses 16 and are incident on the finger touching surface 22b at an angle that is greater than the critical angle (that is, greater than 41.2°) for glass and water. In one embodiment that has been tested, the angle of the interrogating light beams 18, 20 are sixty degrees (60°) to the normal at the surface 22b and thus well above the critical angle. This means that all of the light incident on the valley zones is reflected off at a mirror image angle and thus exits from the opposite side surface 22s in a direction completely away from the imaging lens 24. In that design, it is convenient for the side surfaces 22s of the platen to be at an angle of 60° to the back surface 22b so that the interrogating light beams 18, 20 are essentially normal to a side 22s of the platen 22. This angular relationship is desirable but not critical as long as the interrogating light beams are incident on the touching surface 22b at an angle greater than the critical angle.

Although the axis 33 of the imaging segment composed of the imaging lens 24 and CCD array 26 is normal to the finger touching surface 22b of the platen, the axis 33 could be positioned at any angle in a substantial zone which zone is bordered by the axis of the interrogating light beams 18, 20 and the mirror axis of those interrogating light beams.

The interrogating light 18, 20 is incident at the ridges and reflected in a scattered fashion so as to provide the modulated light 23 which is imaged by the lens 24 on the array 26.

The liquid 34 serves to enhance both valley and ridge presence. The key way in which the liquid 34 enhances ridge presence is by filling in scratches and holes so that a uniform ridge zone scatters light. This provides a brighter and more continuous ridge zone image.

The key way in which the valley is enhanced is because of the presence of the trapped air in the valley zones which serves to hold the valleys open and avoid valley closure that does occur in a number of circumstances. Thus the presence and continuity of the valleys is enhanced. The combined result of ridge and valley enhancement is an improved signal to noise ratio. As best seen in FIG. 4, the air pockets 36 define the valley zones and the liquid contact with the ridges defines the ridge zones.

The incident interrogating light beams 18, 20 are at an angle to the normal at the surface 22b great enough so that light which impinges on the interface between the air pockets 36 and the liquid 34 will be reflected at a mirror angle out a side 22s of the platen 22. Thus the angle to the normal of the incident light beam must be greater than the critical angle for the liquid 34 as well as for the platen 22.

Applicant has found that a number of liquids will adequately perform the function required including water and alcohol. At present, applicant prefers alcohol, not because it gives a better image, but because it dries more quickly on the individual's finger, it is antiseptic and is easy to handle.

The layer of liquid, water or alcohol or whatever, must be thick enough to immerse the ridges and also form the air pockets 36 that define the valley zones. Compared to the techniques of misting a finger, this is in effect the creation of a well of water. This well of water has been found to be adequately deep as a layer formed on the surface and held by the surface tension of the water or alcohol.

It has been known that moist fingers which are moistened either by misting with water or through finger oil adhere better to the platen and provide a better image. It should be noted that misting does not create this liquid-to-air interface in the valleys and, indeed, if misting were to cause water to enter the valley zones, it would defeat the creation of an image. This invention contrasts with such an arrangement in that in this invention the ridge zones are entirely immersed in the liquid and the valley zones are defined by a pocket of air 36 which pocket of air is trapped in the valley zone by the liquid involved so as to provide better definition for the valley zone. The pocket of air defines a valley air-to-liquid interface boundary that is above the surface of the platen.

Applicant believes that there is probably no upper limit to the thickness of the liquid layer, apart from convenience, as long as the layer is thick enough to perform this function of immersing the ridges and trapping an air pocket in the valley zones. A finger could be entirely immersed in water and this enhancement effect should be obtained as long as the liquid-to-air interface in the valleys obtains.

Accordingly, what is important is that the layer of liquid is thick enough so that a liquid-to-air interface is formed in the valley zones.

The FIGS. illustrate one preferred embodiment in which two interrogating light beams are used to assure that the ridge zone which reflects scattered light include certain ridge areas that might not otherwise scatter light toward the lens 24. For example, a ridge in alignment with the direction of an incident light beam would not scatter the incident light in the same way as does a ridge at a non-parallel angle to that beam. Use of two or more interrogating beams having non-parallel axes assures an equally bright ridge image for ridges having any geometric orientation. This dual beam 18, 20 embodiment is particularly adapted for use in identification systems because it will provide an image of all minutia.

However a single interrogating beam 18 could be used to provide an image, though some minutia might be omitted. Such an embodiment might prove adequate in many access system applications.

Three angled edges 22s are illustrated. The fourth edge is not angled to avoid having the finger touching surface too far inboard from the edge on which the finger rests. However, the light from the beam 20 that is reflected from the valleys, exits from the orthogonal back side at an angle such that even with a degree of bending, it substantially steers away from the lens 24.

The light sources in all of these embodiments may be either an incandescent lamp or a light emitting diode.

In general terms, the dual interrogating light beam embodiment will provide an image with a larger number of minutia than if only one light source is used. Some additional enhancement of the image can be obtained with a third interrogating light beam from the other side of the finger being examined.

In an embodiment where four fingers are applied to a platen, the dimensions of the platen have to be different. In one embodiment that has been tested, such a platen was two inches thick in order to accommodate interrogating light beams wide enough to encompass all four fingers. In that embodiment, the upper surface was approximately six inches long across the fingers to be applied and three inches deep along the length of the fingers. In that embodiment, the surface from which the modulated light emerges was approximately four inches by two inches.

In circumstances where a finger is rolled across the platen in order to obtain a nail-to-nail fingerprint, it has been noticed that there is a tendency for a finger to slip or slide on the platen. When this occurs, it can either reduce information available or provide a completely useless image. What has been noticed is that when there is a liquid such as water or alcohol or a mixture thereof on the platen in which the finger is immersed, this slide or slip problem does not occur.

The primary mechanism by which this improvement operates, particularly in the preferred embodiment, is, as described above, one in which light reflected from the air-liquid interface is steered entirely away from the CCD array and scattered light from the ridges is imaged at the CCD array so as to provide a strong contrast between ridge and valley zones. There are other mechanisms which appear to be at work and which may have more or less effect depending on the embodiment involved.

For example, if only a single interrogating light beam, such as the light beam 18, is employed, the ridge shadows the valley, and to the extent shadowing occurs, it will reinforce the primary mechanism discussed above.

In addition, to the extent that liquid reaches up into what would normally be called the valley zone, it provides a longer path for the reflection of light off valley surfaces. This longer path in a liquid medium produces a greater degree of scattering than occurs along what might nominally be called the ridge zones. In addition, the valley zone surface tends to be more irregular than the ridge zone surface so that any possible reflection off the valley surfaces will tend to scatter more than off the ridge surfaces. To the extent that this greater degree of scattering because of greater path length through the liquid and greater valley zone surface irregularity occurs, it is a phenomenon which causes ridge valley distinction because of rejection by the system lens of the higher order angular scatter from the valleys and thus reinforces the primary mechanism discussed above.

Accordingly, it should be understood that this immersion in liquid technique has the advantage that various mechanisms for distinguishing between ridge and valley zones tend to reinforce one another rather than cancel one another.

Although applicant is not completely sure as to all of the mechanisms involved in why this finger immersion in liquid provides an improved result, applicant has come to believe that another part of the reason has to do with the manner in which liquid interacts with the finger tissue. The result might be either a tauter surface skin or a lightly more swollen ridge, or either both of which would reduce the incidence of cracks along the ridges that might interfere with a smooth image.

In any case, applicant now hypothesizes that the enhanced results may be for a combination of a substantial number of mechanisms, including (a) the air pocket holding open the valley zones, (b) the steering of light reflected from the liquid-to-air interface that defines the valley zone away from the imaging array, (c) an enhanced shadowing of the valleys by the ridges, (d) differential scattering of ridges and valleys due to differential light path length in the liquid involved, (d) the complete or partial filling in of certain ridge cracks with the liquid, and (f) a smoother finger ridge due to interaction with the liquid.

The relative significance of each of the mechanisms or even the relevance of a particular mechanism, will be a function of the optical system employed. A preferred embodiment has been disclosed. But applicant believes that the immersion of the finger in water, as defined herein, can be employed to enhance the image in a wide variety of optical imaging systems even through particular ones of the above listed mechanisms may not be relevant to the optical system involved.

What is claimed is:

1. In an optical fingerprint imaging system having at least one interrogating light beam for illuminating a finger placed against a finger touching surface of a platen to provide a modulated light beam, the system having an imaging segment for imaging the modulated beam onto a photo-electric transducer, the improvement comprising:

a layer of liquid on the finger touching surface of the platen, said layer of liquid being thick enough to assure that the ridge zones of a finger on said finger touching surface are immersed in said liquid.

the photo-electric transducer receiving scattered light from the ridges of a finger placed against the liquid covered touching surface of the platen.

2. The system of claim 1 wherein said liquid has an index of refraction similar to that of the material of said platen.

3. In the method of providing an optical fingerprint image including the steps of applying an interrogating light beam to illuminate a finger placed against a finger touching surface of a platen and thereby providing a modulated light beam and imaging the modulated light beam onto a photo-electric transducer, the improvement comprising the steps of:

applying a layer of a liquid to the finger touching surface of said platen, immersing the finger whose image is to be taken in said liquid layer, and imaging the scattered light from the ridges at the photo-electric transducers.

4. The system of claim 3 wherein said liquid has an index of refraction similar to that of the material of said platen.

5. In the method of providing an optical fingerprint image including the steps of applying an interrogating light beam to illuminate a finger placed against a finger touching surface of a platen and thereby providing a modulated light beam and imaging the modulated light beam onto a photo-electric transducer, the improvement comprising the step of:

immersing a finger in a layer of liquid on the finger touching surface of the platen and contacting said finger touching surface with the finger so immersed.

6. The method of claim 5 further comprising the step of:

applying said interrogating light beam to the finger touching surface such that the axis of said interrogating light beam has an angle to the finger touching surface greater than the critical angle.

7. In the method of providing an optical fingerprint image including the steps of applying an interrogating light beam to illuminate a finger placed against a finger touching surface of a platen and thereby providing a modulated light beam and imaging the modulated light beam onto a photo-electric transducer, the improvement comprising the step of:

rolling a finger across the finger touching surface of the platen while the finger is immersed in a layer of liquid on said finger touching surface of said platen.

8. The method of claim 7 further comprising the step of:

applying said interrogating light beam to the finger touching surface such that the axis of said interrogating light beam has an angle to the finger touching surface greater than the critical angle.

* * * * *